United States Patent
Bouten et al.

(10) Patent No.: US 7,117,720 B2
(45) Date of Patent: Oct. 10, 2006

(54) METHOD FOR MEASURING A PERMEATION RATE, A TEST AND AN APPARATUS FOR MEASURING AND TESTING

(75) Inventors: Petrus Cornelis Paulus Bouten, Eindhoven (NL); Giovanni Nisato, Eindhoven (NL); Peter Jan Slikkerveer, Eindhoven (NL); Henricus Franciscus Johannus Jacobus Van Tongeren, Eindhoven (NL); Eliav Itzhak Haskal, Eindhoven (NL); Paul Van Der Sluis, Eindhoven (NL)

(73) Assignee: Koninklijke Philips Electronics N. V., Eindhoven (NL)

( * ) Notice: Subject to any disclaimer, the term of this patent is extended or adjusted under 35 U.S.C. 154(b) by 0 days.

(21) Appl. No.: 11/298,651

(22) Filed: Dec. 12, 2005

(65) Prior Publication Data

US 2006/0147346 A1 Jul. 6, 2006

Related U.S. Application Data

(63) Continuation of application No. 10/106,951, filed on Mar. 26, 2002, now Pat. No. 6,993,956.

(30) Foreign Application Priority Data

Mar. 29, 2001 (EP) ................. 01201229
Jan. 17, 2002 (EP) ................. 02075202

(51) Int. Cl.
*G01M 3/04* (2006.01)
*G01N 15/08* (2006.01)
*G01N 21/77* (2006.01)
*G01D 21/00* (2006.01)

(52) U.S. Cl. ................. 73/40; 73/38; 436/169; 116/206

(58) Field of Classification Search ................. 73/38, 73/40; 436/169, 170; 116/206; 702/81, 702/84, 31, 32, 33, 34, 35, 40
See application file for complete search history.

(56) References Cited

U.S. PATENT DOCUMENTS

| | | | |
|---|---|---|---|
| 4,326,514 A | 4/1982 | Eian | |
| 4,822,743 A | 4/1989 | Wegrzyn | |
| 4,848,138 A | 7/1989 | Marshall | |
| 4,987,849 A | 1/1991 | Sherman | |
| 5,001,346 A | 3/1991 | Barkhoudarian | |
| 5,009,218 A | 4/1991 | Bachli | |
| 5,047,947 A | 9/1991 | Stump | |
| 5,128,106 A | 7/1992 | Buschmann et al. | |
| 5,323,774 A | 6/1994 | Fehlauer | |
| 5,447,688 A | 9/1995 | Moore | |
| 5,449,912 A | 9/1995 | Mayer | |
| 5,926,262 A | 7/1999 | Jung et al. | |
| 5,951,909 A | 9/1999 | Verdicchio et al. | |
| 5,963,881 A | 10/1999 | Kahn et al. | |
| 6,259,370 B1 | 7/2001 | Takenoshita | |
| 6,622,059 B1 | 9/2003 | Toprac et al. | |
| 6,993,956 B1 * | 2/2006 | Bouten et al. ................. | 73/40 |
| 2001/0034063 A1 | 10/2001 | Saunders et al. | |

(Continued)

FOREIGN PATENT DOCUMENTS

EP 0629497 A2 12/1994

(Continued)

*Primary Examiner*—Michael Cygan (57) ABSTRACT

A method is proposed for measuring water permeability of substrates (1). A reactive compound (Ca, Ba) which reacts with a diffusing material, e.g. water, is applied on the substrate and the change in time of transmissivity, reflectivity of the layer is monitored in time.

20 Claims, 5 Drawing Sheets

U.S. PATENT DOCUMENTS

2003/0014205 A1    1/2003    Tabor

FOREIGN PATENT DOCUMENTS

| JP | 60020135 | 1/1985 |
| JP | 361031937 A | 2/1986 |
| JP | 62032336 A | 2/1987 |
| JP | 402306132 A | 12/1990 |

* cited by examiner

METHOD FOR MEASURING A PERMEATION RATE, A TEST AND AN APPARATUS FOR MEASURING AND TESTING

This application is a continuation of U.S. patent application Ser. No. 10/106,951, "A METHOD FOR MEASURING A PERMEATION RATE, A TEST, AND AN APPARATUS FOR MEASURING AND TESTING" filed on 26 Mar. 2002 now U.S. Pat. No. 6,993,956 in the names of Petrus C. P. Bouten et al.

The invention relates to a method for measuring the permeation rate of a substrate, especially a flexible substrate such as a polymer (plastic) substrate for use in liquid crystal display devices, polyLED and other (organic) LED display devices. Especially the combination of polymer (plastic) substrates and (organic) LED devices is very attractive because all materials are flexible and the LED devices have excellent viewing angle properties.

However the electroluminescent organic materials are easily oxidized and react with water. For the cathode material usually reactive metals are used, which degrade even faster. For this reason in the state of the art glass is used as a substrate, which is highly impermeable. The main concern related to permeability here resides in the permeation rate of the seal line. In LCD's the water may react with the liquid crystal material.

Although commercial test systems for measuring the permeation rate of a substrate are available from firms like Mocon (Modern Controls), these are limited to lower limits of $10^{-3}$ g/m$^2$/day for water and $10^{-3}$ cc/m$^2$/day/bar for oxygen (at standard temperature and pressure). For plastic substrates to be used in liquid crystal display devices and (organic) LED display devices this value should be at least a factor of 100 lower. Moreover tests can take as long as a week, which is unacceptable in a production environment. The same holds for testing a (semi) finished product.

The invention has as its purpose to solve one or more of these problems To this end it provides a method for measuring a permeation rate, a test method and an apparatus for measuring and testing in which permeation rates as low as $10^{-5}$ g/m$^2$/day for water or even lower can be measured.

To this end a method according to the invention comprises the steps of a) applying a layer of a reactive material to a first side of the substrate in an substantially inert atmosphere b) positioning said first side of the substrate within a substantially hermetically sealed environment c) exposing the other side of the substrate to an environment containing compounds which react with the reactive material and d) comparing the light reflectivity or the light absorption of the layer of refactive material with a calibration value.

The invention is based on the insight that because of e.g. oxidation due to the presence of water and oxygen a reactive material like barium or calcium evolves to an increasingly transparent layer. The transmission or reflection characteristics of the layer can be measured and for instance by storing successive measurements (e.g. CCD images) image analysis, like grey value determination, can be used to determine the thickness of the residual metal layer, which is related to the amount of absorbed compounds, especially water. So these transmission or reflection characteristics are directly related to the permeation rate.

The method according to the invention has the advantages of faster testing. Moreover it provides a greater sensitivity at least in the testing of water. permeability. Also it is more efficient than the existing test methods and the test apparatus can be more flexible In certain cases, e.g. when a substantially impermeable substrate (metal or glass) is tested, permeability of a seal or a sealing rim on the substrate may determine the permeation rate. It will be clear that in this case in the claims "substrate" is meant to comprise said seal or a sealing rim. To prevent the permeability testing to be influenced by the permeability of a seal or a sealing rim a sealing rim having more walls is used if necessary. Providing a getter in a double walled seal can prevent further sensibility to penetration through said walls. The reactive material used for the test can be used as getter when applied between the two seal rings.

In a test method according to the invention at least one sample substrate is tested with said method and discriminating between batches to have them pass or not pass the test is based on a threshold value of the permeation rate. The threshold value may either be a mean value or be an extreme value of the permeation rate within a batch.

An apparatus according to the invention comprises a) a first chamber in which an substantially inert atmosphere can be generated b) means for introducing a reactive material into said chamber c) means for positioning said first side of the substrate within a substantially hermetically sealed environment d) means for exposing the hermetically sealed environment to compounds which react with the reactive material e) means for comparing the light reflectivity or the light absorption of the reactive material with a calibration value It appears that the test method on the other hand can be used for testing the permeability of encapsulations, like seals, lids or measurement capsules.

In practice the different steps will be divided over several sub-apparatuses.

These and other aspects of the invention will be discussed in more detail with reference to several embodiments and the drawings in which

FIG. 11 shows another embodiment according to the invention, while

Figures are not drawn to scale while in general like reference numerals identify like elements The principle of the method for measuring the permeation rate of a substrate will be discussed with reference to FIGS. 1–6. A thin layer 2 (e.g. 100 nm) of a reactive material, in this example Ca, is deposited in an substantially inert atmosphere on a substrate 1 to be tested. In this example the Ca is deposited in a pattern of 16 squares. A glass sheet or lid 3 is interconnected to the substrate 1 along its edge via a substantially hermetic seal 4, e.g. a glue, a metal like In or a solder metal to form a closed box. Alternatively the Ca layer may be covered by a hermetic coating (silicon nitride, silicon oxide or a metal layer (to provide a hermetic sealing of said layer.

Water or oxygen permeating into the box reacts with Ca according to the reactions $$Ca+H_2O \rightarrow CaO+H_2 \quad (1)$$

$$CaO+H_2O \rightarrow Ca(OH)_2 \quad (2)$$

or $$2\ Ca+O_2 \rightarrow 2CaO \quad (3)$$

Due to these reactions the amount of calcium decreases leading to a smaller metal layer thickness (or a reduced area of the deposited material). This also implies that the deposited layer becomes transparent, the transparency or transmission being an indicator for the amount of water or oxygen having diffused into the box.

Figure 3:
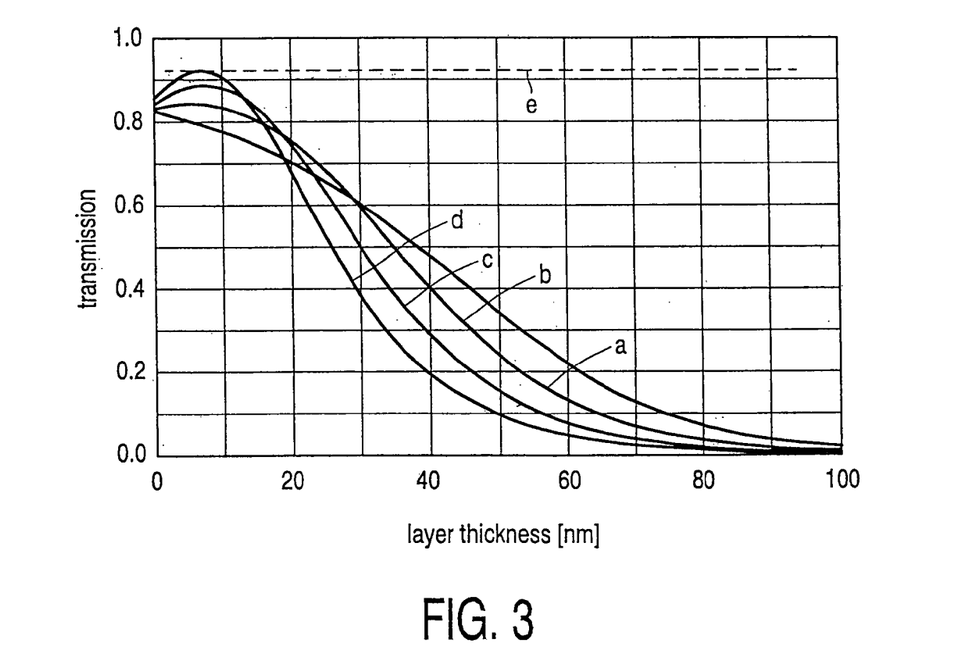
FIG. 3 shows transmission curves for a CaO/Ca layer on glass for different wavelengths as a function of the layer thickness.
Figure 4:
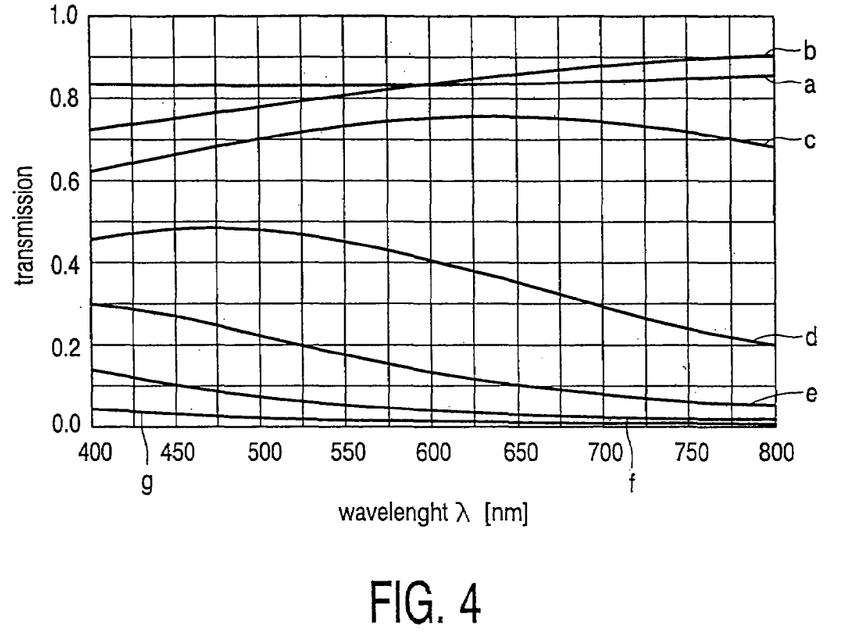
FIG. 4 shows transmission curves for a CaO/Ca layer on glass for different values of the layer thickness as a function of the wavelength.

FIG. 3 shows calculated transmission curves for a CaO/Ca layer on glass for different wavelengths, viz. 500 nm (curve a), 600 nm (curve b), 700 nm (curve c), 800 nm (curve d) and the substrate 1 (curve e), as a function of the layer thickness. Since the layer thickness is in the order of the wavelength of light the transmission or reflection of the layer the transmission and reflection of the layers depend strongly on the wavelength too. This is shown by way of example in FIG. 4, which shows calculated transmission curves for a CaO/Ca layer on glass for different values of the layer, viz. 0 nm (curve a), 10 nm (curve b), 20 nm (curve c), 40 nm (curve d), 60 nm (curve e), 80 nm (curve f) and 100 nm (curve g), as a function of the wavelength.

Figure 5:
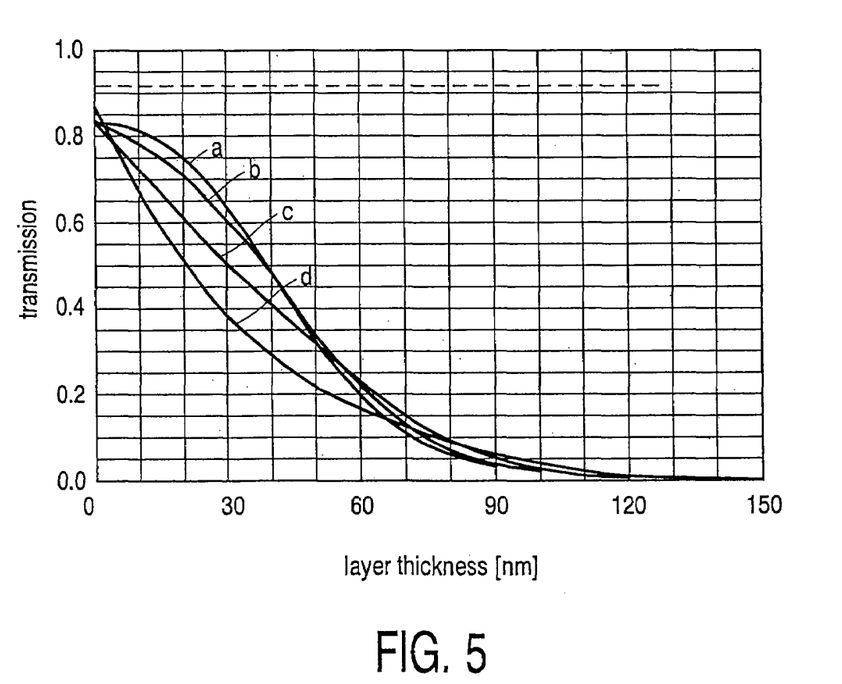
FIG. 5 shows transmission curves for a CaO/Ca layer on glass for λ=500 nm as a function of the layer thickness for different values of the original layer thickness.

FIG. 5 shows transmission curves for a CaO/Ca layer on glass at a fixed wavelength as a function of the layer thickness for different values of the original layer thickness. In FIG. 5 this is shown for $\lambda=500$ nm for layers having an original layer thickness of 90 nm (curve d), 100 nm (curve e), 120 nm (curve g), and 150 nm (curve i)

These data can be used to determine a calibration curve to be used during measuring and testing dependent on the wavelength used and the original layer thickness. Said curve can be stored as a function relating the transmission or reflection to a certain layer thickness. The intermediate values of transmission or reflection can be measured as (average) grey-values by means of a CCD device or a digital camera. To obtain reference values a black border is introduced in the device of FIG. 1 to measure the transmission of an average black area; the reference value for average white is determined by measuring the transmission of the transmissive area between the squares of deposited Ca.

Since the thickness of the original Ca layer as well as the total area is known a (difference in) grey-value can be attributed to a (difference in) layer thickness. The total amount of Ca having reacted according to reactions (1), (2) and (3) and the amount of water required to convert the residual calcium volume is known. This is shown for a number of samples in FIG. 6, which shows the residual calcium volume as a function of time. The difference between two moments of measuring determines the difference in grey-values between said two moments of measuring. This is shown for a number of samples (substrates of different kinds of substrate materials) in FIG. 6. The slope of a curve is a measure for the permeation rate.

Figure 6:
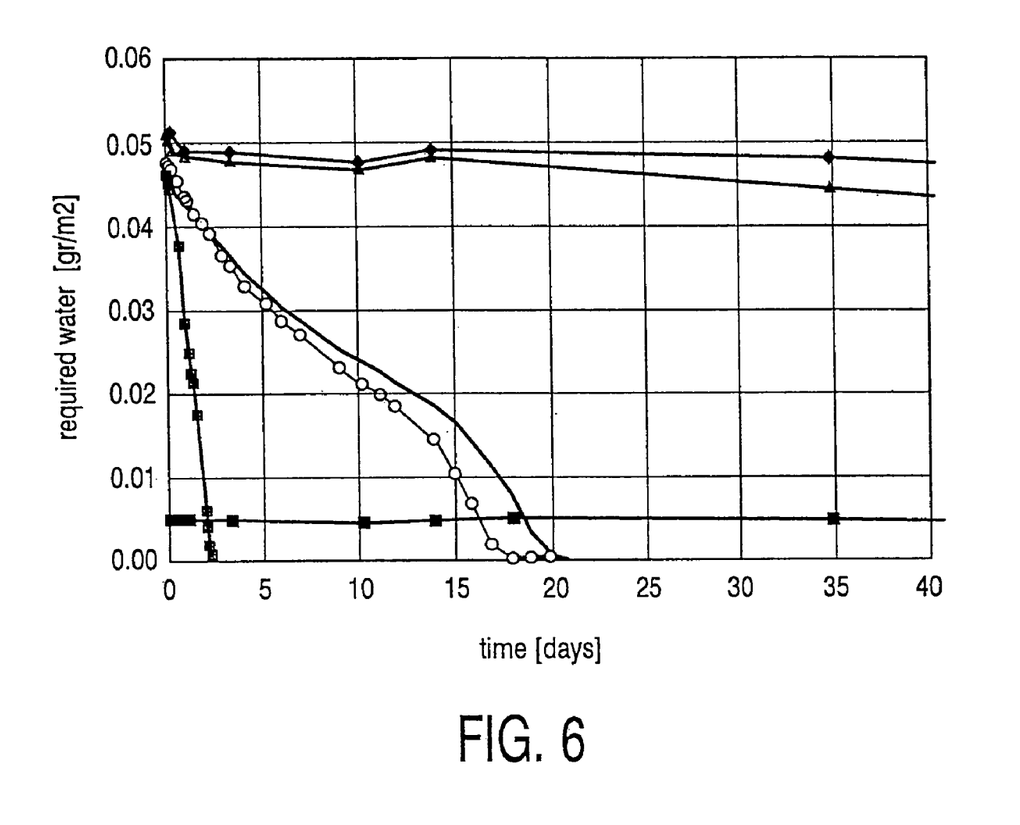
FIG. 6 shows the results of some sample tests.

The sample of curve c shows a permeation rate of about $2.10^{-3}$ g/m²/day for water, whereas the sample of curves e and f show permeation rates of about $2.10^{-4}$ g/m²/day for water and sample of curve d shows a permeation rate of $<10^{-5}$ g/m²/day for water. This shows that the method can measure permeation rates up to a factor 100 or more better than existing equipment. Similar experiments show that the method is suitable for testing oxygen permeability to a level of $10^{-2}$ cc/m²/day/bar or lower.

Figure 7:
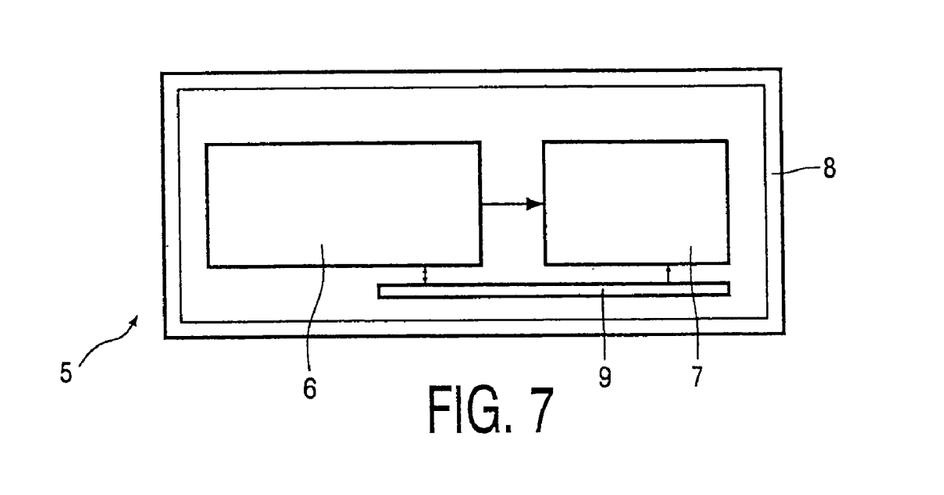
FIG. 7 shows a schematic embodiment of a measuring and testing equipment for measuring or testing the permeation rate.

FIG. 7 shows a measuring and testing equipment 5 for measuring or testing the permeation rate in which means 6 for obtaining a sample substrate and a device 7 for measuring the light reflectivity or the light absorption of a layer are both present within the same substantially hermetically sealed environment, for example a glove box 8 with manipulating means 9. In another embodiment the means 6 for obtaining a sample substrate and the device 7 for measuring the light reflectivity or the light absorption of a layer may be placed in different glove boxes 8, provided the samples can be transported from the means 6 for obtaining a sample substrate to the device 7 for measuring in a substantially hermetically sealed environment.

A sample substrate is obtained by calcium deposition of a predetermined thickness, e.g. 100 nm, using a mask. (see FIG. 8, in this example a 4×4 array of 6 mm² is used). Calcium covered samples can be stored in the glove box, but preferably the test cells are manufactured as soon as possible after deposition together with reference cells if any.

Figure 8:
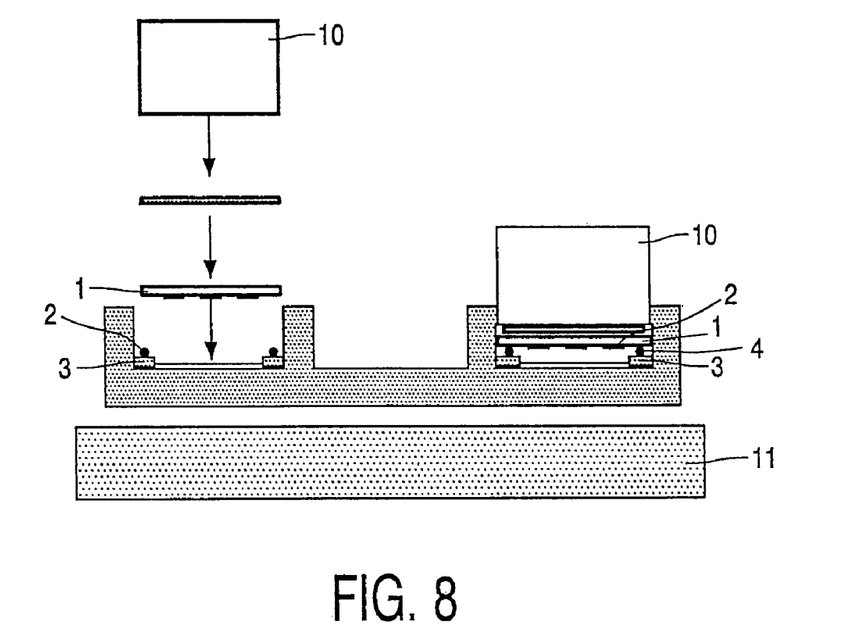
FIG. 8 shows means for obtaining a sample substrate within a substantially hermetically sealed environment.

The substrates is placed upside down on the lid 3, which has been provided with a seal 4. To obtain a good sealing a copper weight 10 is placed on top of the assembly, while the whole assembly is heated on a heating plate 11 at 100° C. for 15 minutes. To prevent the substrate from sticking to the copper plate a Teflon spacer 12 may be inserted temporarily. It will be clear that the above figures are just an example and may be different dependent on the materials used.

Figure 9:
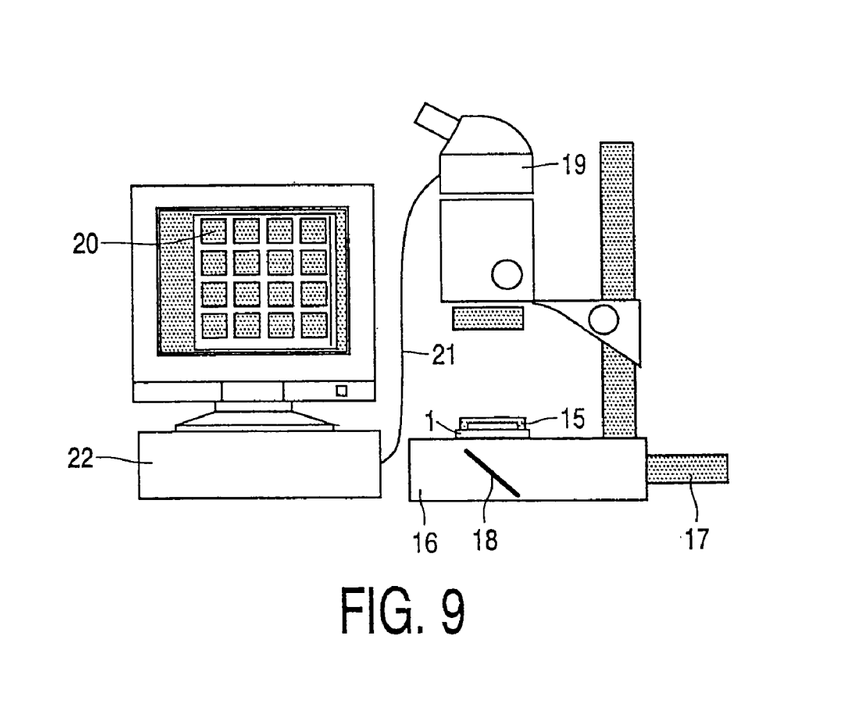
FIGS. 9 and 10 show embodiments of devices for measuring the light reflectivity or the light absorption of a layer.

FIG. 9 shows in more detail a possible device 7 for measuring the light transmission of a CaO/Ca layer on glass in a sample as prepared with reference to FIG. 8, which sample is exposed to an H₂O atmosphere. The sample 15 is placed on top of an optical system 16, which is illuminated by means of fiber illumination via a fiber 17. The light passes the sample via a mirror 18 and digital images are taken by means of a digital camera 19. The images 20 may be taken on a continuous base and are stored via interconnections 21 in a computer or dataprocessing equipment 22.

Figure 10:
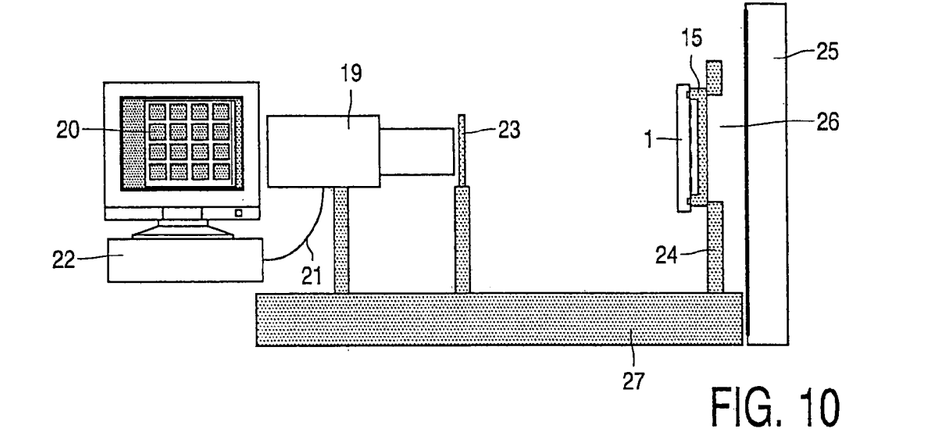

FIG. 10 shows another implementation in which the transmission is measured for a single colour by introducing a colour filter 23. The sample 15 is now vertically placed within a hole 26 in a support 24 and is illuminated by means of a backlight 25. The camera 19 is in this example a CCD camera optimized for the colour used. The camera 19, a colour filter 23 and the support 24 are placed on an optical rail 27.

Image processing of the obtained grey-values can be performed in different ways. As mentioned above, a calibration curve can be determined in advance, as is shown with reference to FIGS. 3–5. Other methods such as deconvolution of spectra are also possible.

It is clear from the above that different steps of the method preferably are performed in dedicated sub-apparatuses, such as a first sub-apparatus for deposition, a second one for exposing to environmental conditions and a third one for measuring, although some of these may be combined e.g. in the case of continuous monitoring of the Ca layer, which may be useful when testing is performed at elevated temperatures.

Figure 1:
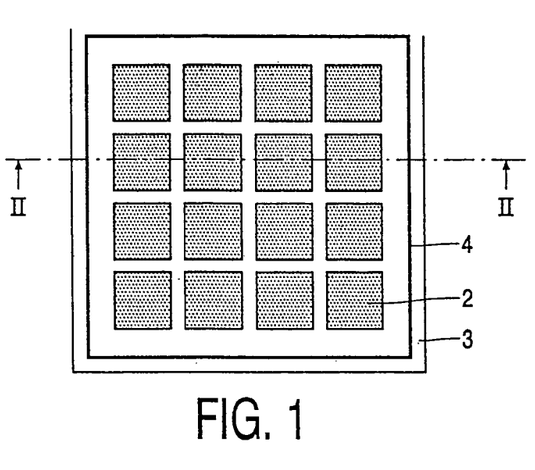
FIG. 1 shows a plane view of a sample substrate within a substantially hermetically sealed environment
Figure 2:
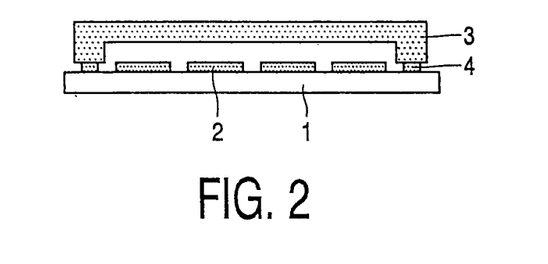
FIG. 2 shows a cross section along line II—II in FIG. 1.
Figure 11:
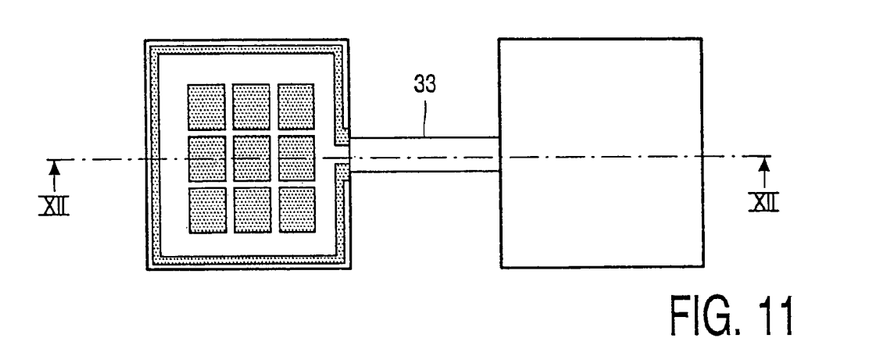
Figure 12:
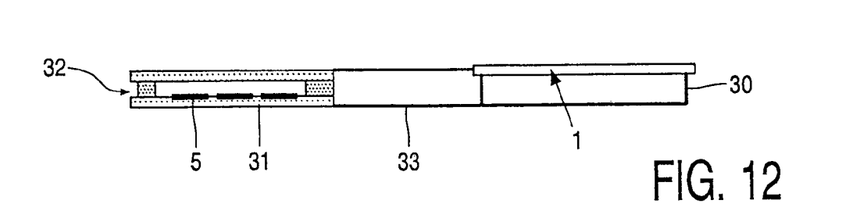
FIG. 12 shows a cross section along line XII—XII in FIG. 11

FIGS. 11 and 12 finally show another implementation in which a (non-transparent) substrate 1 is sealed to a housing 30, comparable to the lid 3 in FIGS. 1, 2, whereas the Ca pattern 3 now has been deposited on a transmissive substrate 31 of a measuring cell 32. To start measuring or testing the housing 30 is interconnected to the measuring cell 32 via a glass tube 33. Water or oxygen permeating into the housing 30 via substrate 1 passes the tube 33 and reacts with Ca. The Ca layer is affected in a similar method as mentioned above. The transparency of the layer is measured again for example in a similar method as shown with respect to FIGS. 9, 10 to determine the permeation rate.

In some cases, if the substrates have very small permeability the leaking of the seal sets the lower boundary of the sensitivity of the measurement method.

Figure 13:
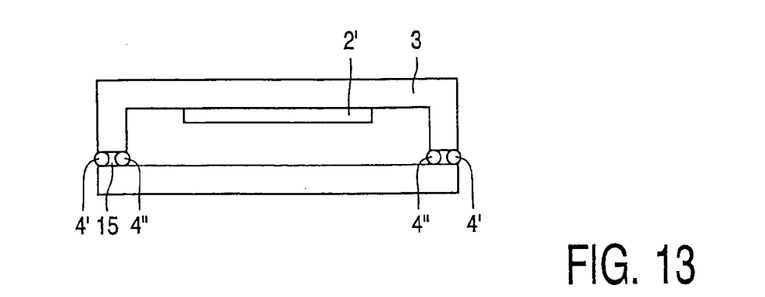
FIG. 13 shows another example of using the invention.

In this case the seal is split in two walls (an outer wall 4' and an inner wall 4'', as shown in FIG. 13 for a measurement to be discussed below). Between these two walls a cavity is created where a getter (desiccant) 15 is placed. If for the desiccant the same reactive material that as for the measurement, is chosen they can be applied in the same process step.

In case of the permeability test cells, now it is possible to use a desiccant to absorb the leaking water and oxygen through the seal. Since, when using Ca as an indicative layer 2 the Ca in the main cavity also acts as a getter, substantially no concentration gradient is present over the inner seal, so there is no water and oxygen transport through this seal The making of two chambers in the seal does not have to be an additional step, e.g. when using a glass lid, where the cavities are made by powderblasting.

It should be noted that the above-mentioned embodiments illustrate rather than limit the invention, and that those skilled in the art will be able to design many alternative embodiments without departing from the scope of the appended claims. In this respect it should be noted that also the measure of reflection of the layers is an indication for its thickness and can be used to determine the permeation rate. Another reactive material like barium or natrium can be used in stead of calcium.

An example is gadolinium which is very suitable for the testing of permeation of hydrogen. In the method according to the invention now the layer 2 comprises a stack of metals, e.g. Gd/Pd or $Mg_xGd_{1-x}$/Pd. The reactive compound reacts well with diffusing hydrogen. The reaction leads to a change in the appearance of the layer again. For hydrogen detection a catalyst might be necessary. This means that instead of a single Ca-layer a stack of two layers is deposited, for instance 100 nmGd+10 nm Pd. For a surface area of 1 $cm^2$ this represents $5.10^{-7}$ mole Gd. This silvery Gd reacts to dark blue $GdH_2$. The change in colour is measured again as a change in reflection (or transmission. If $5.10^{-7}$ mole $H_2$ reacts in 1 day this represents a hydrogen flux of $10^{-2}$ g $H_2$ per day per $m^2$. Hydrogen fluxes between $10^{-4}$ and $10^2$ g H2 per day per $m^2$ can be measured with this set up.

Since in normal ambient hydrogen is present at extremely low concentrations all work can be carried out in normal ambient. The Pd layer not only acts as a catalyst but also protects the Gd from corrosion in air. The insensitivity of the indicator metal layer makes this method very suitable for making half fabricates for the metod or for an apparatus according to the invention, like ready-to-use cover lids 3 (with indicator metal layer 2', See FIG. 13) or measuring cells 32.

It goes without saying that the method is also applicable for testing substrates and encapsulations outside the display applications, for example testing on a sample base of PolyLed/OLED lids and OLED seal materials, IC lids or in medical applications.

In the claims, any reference signs placed between parentheses shall not be constructed as limiting the claim. The word "comprising" does not exclude the presence of other elements or steps than those listed in a claim.

The invention claimed is:

1. A method of measuring a permeation rate of a substrate, comprising:
   obtaining a series of calibration values, each calibration value corresponding to a specific percentage of light having a first wavelength transmitted through or reflected by a substrate coated with a reactive material for a different thickness of the reactive material;
   applying a layer of the reactive material to a first side of the substrate;
   sealing the first side of the substrate within a substantially hermetically sealed environment;
   exposing a second side of the substrate opposite the first side of the substrate to an environment containing at least one substance which reacts with the reactive material;
   measuring a percentage of light having the first wavelength transmitted through or reflected by the layer of reactive material; and
   comparing the percentage of light having the first wavelength transmitted through or reflected by the layer of reactive material, against the series of calibration values, to determine the permeation rate of substance through the substrate.

2. The method of claim 1, wherein the reactive material includes at least one of barium, calcium and sodium, and gadolinium.

3. The method of claim 1, wherein percentage of light having the first wavelength transmitted through or reflected by the layer of reactive material is measured as a grey-value.

4. The method of claim 1, wherein the second side of the substrate is exposed to a controlled environment.

5. The method of claim 1, wherein the substance is water.

6. The method of claim 1, wherein the substance includes one of oxygen gas and hydrogen gas.

7. The method of claim 1, wherein sealing the first side of the substrate within a substantially hermetically sealed environment comprises:
   placing the substrate on a lid provided with a sealing material, the first side of the substrate confronting the lid;
   applying pressure to one of the lid and the substrate to obtain a seal between the substrate and the lid; and
   applying heat to set the seal between the lid and the substrate.

8. The method of claim 1, wherein the layer of the reactive material is applied to the first side of the substrate in a substantially inert atmosphere.

9. A method of measuring a permeation rate of a first, opaque substrate, comprising:
   obtaining a series of calibration values, each calibration value corresponding to a specific percentage of light having a first wavelength transmitted through or reflected by a substrate coated with a reactive material for a different thickness of the reactive material;

sealing a first side of the first, opaque, substrate within a substantially hermetically sealed environment;

coating a layer of reactive material onto a first side of a second, optically transmissive, substrate, said first side of the second, optically transmissive, substrate also being sealed within the substantially hermetically sealed environment;

exposing a second side of the second, optically transmissive, substrate opposite the first side of the second, optically transmissive, substrate to an environment containing at least one substance which reacts with the reactive material;

measuring a percentage of light having the first wavelength transmitted through or reflected by the layer of reactive material; and comparing the percentage of light having the first wavelength transmitted through or reflected by the layer of reactive material, against the series of calibration values, to determine the permeation rate of substance through the substrate.

10. The method of claim 9, wherein the reactive material includes at least one of barium, calcium and sodium, and gadolinium.

11. The method of claim 9, wherein the percentage of light having the first wavelength transmitted through or reflected by the layer of reactive material is measured as a grey-value.

12. The method of claim 9, wherein the second side of the substrate is exposed to a controlled environment.

13. The method of claim 9, wherein the substance is water.

14. The method of claim 9, wherein the substance includes one of oxygen gas and hydrogen gas.

15. An apparatus for measuring a permeation rate of a substrate, comprising:

sample device producing means for applying a layer of the reactive material to a first side of a substrate and sealing the first side of the substrate within a substantially hermetically sealed environment;

a measurement device for measuring a permeation rate of the substrate by, exposing a second side of the sample substrate opposite the first side of the substrate to an environment containing at least one substance which reacts with the reactive material, measuring a percentage of light having the first wavelength transmitted through or reflected by the layer of reactive material, and comparing the percentage of light having the first wavelength transmitted through or reflected by the layer of reactive material, against the series of calibration values, to determine the permeation rate of substance through the substrate.

16. The apparatus of claim 15, wherein the sample device producing means and the measurement device are disposed within a glove box.

17. The apparatus of claim 15, wherein the sample device producing means includes:

a fixture holding a lid for the sample device;

means for applying pressure to one of the lid and the substrate to obtain a seal between the substrate and the lid; and means for applying heat to set the seal between the lid and the substrate.

18. The apparatus of claim 15, wherein the measurement device comprises:

an illumination system for illuminating the sample device;

a camera for talking an image of the illuminated sample device; and a computer for analyzing the image to measure the percentage of light having the first wavelength transmitted through or reflected by the layer of reactive material.

19. The apparatus of claim 15, wherein the reactive material includes at least one of barium, calcium and sodium, and gadolinium.

20. The apparatus of claim 15, wherein the substance includes one of water, oxygen gas and hydrogen gas.

* * * * *